US008577064B2

(12) United States Patent
Wax

(10) Patent No.: US 8,577,064 B2
(45) Date of Patent: Nov. 5, 2013

(54) SOUND CAPTURING AND GUIDING SYSTEM FROM STEREO SPEAKERS PACKED TOGETHER IN A CLOSED BOX AND HEARD AS STEREO SOUND COMING FROM VARIOUS DIRECTIONS

(76) Inventor: Omer Arye Wax, Kfar Sava (IL)

( * ) Notice: Subject to any disclaimer, the term of this patent is extended or adjusted under 35 U.S.C. 154(b) by 384 days.

(21) Appl. No.: 12/762,358

(22) Filed: Apr. 18, 2010

(65) Prior Publication Data

US 2010/0266150 A1 Oct. 21, 2010

Related U.S. Application Data

(60) Provisional application No. 61/170,903, filed on Apr. 20, 2009.

(51) Int. Cl.
*H04R 5/033* (2006.01)
*A61B 7/04* (2006.01)

(52) U.S. Cl.
USPC ................................ 381/309; 381/74; 381/67

(58) Field of Classification Search
USPC ............................ 381/309, 67, 74, 73.1, 302
See application file for complete search history.

(56) References Cited

U.S. PATENT DOCUMENTS

| | | | | |
|---|---|---|---|---|
| 5,347,583 | A * | 9/1994 | Dieken et al. | 381/67 |
| 6,220,866 | B1 * | 4/2001 | Amend et al. | 434/266 |
| 8,111,853 | B2 * | 2/2012 | Isvan | 381/337 |
| 2009/0220112 | A1 * | 9/2009 | Fincham | 381/302 |

* cited by examiner

*Primary Examiner* — Duc Nguyen
*Assistant Examiner* — George Monikang
(74) *Attorney, Agent, or Firm* — Mark M. Friedman

(57) ABSTRACT

A stereo speaker sound capturing and guiding system. The system includes devices that connected on each one of the stereo speakers as a cap. The device covers the speaker cones in hermetic way that captures the sound of the specific speaker and don't let the sound mixed with the sound of the other speaker that located in the same closed box or very near to the first speaker. The sound in the cap device guided directly from the speaker through connector facility between the speakers and the user's ears—such as air tubes—and transmitted exclusively to the user's matched ear—the sound from the right speaker gets only to right ear and sound from the left speaker gets only to the left ear—as at least two independent audio channels.

25 Claims, 3 Drawing Sheets

SOUND CAPTURING AND GUIDING SYSTEM FROM STEREO SPEAKERS PACKED TOGETHER IN A CLOSED BOX AND HEARD AS STEREO SOUND COMING FROM VARIOUS DIRECTIONS

TECHNICAL FIELD AND INDUSTRIAL APPLICATION OF THE INVENTION

This application claims the benefit of U.S. Provisional Application No. 61/170,903, filed on 20 Apr. 2009.

BACKGROUND OF THE INVENTION

1. Field of the Invention

This invention relates to stereo speaker sound capturing and guiding system.

The present invention relates particularly to case when the stereo speakers have been packed together in one closed capsule or box or the speakers located very close one to the other and away from the user ears and still the sound from the speakers can be heard as stereo sound that comes from various directions, to the listener ears.

2. Description of Related Art

Stereophonic sound, commonly called stereo, is the reproduction of sound using two or more independent audio channels through a symmetrical configuration of loudspeakers in such a way as to create the impression of sound heard from various directions, as in natural hearing. It is often contrasted with monophonic or "mono" sound, where audio is in the form of one channel.

As a result of the above description, if we packed together two stereo speakers or more in one closed capsule or box or the speakers located very close one to the other and away from the user ears, when we play stereo sound in the speakers, we expect that the stereo sound coming from the speakers will mixed together and the user can not listen to the sound as a stereo sound that come out from at least two independent audio channels and heard from various directions, as the sound doesn't arrive to each ear from a matching separate speaker—right speaker to right ear and left speaker to the left ear and the stereo sound will be heard like mono sound to the user.

SUMMARY OF THE INVENTION

At least two stereo speakers that packed together in one closed capsule or box or the speakers located very close one to the other and away from the user ears.

In this situation, when we play stereo sound in the speakers, we expect that the stereo sound coming from at least two speakers will mixed together and the listener cannot listen to the sound as a stereo sound that come out from at least two independent audio channels and heard from various directions, as the sound doesn't arrive to each ear from a matching separate speaker—right speaker to right ear and left speaker to the left ear. Instead, the sound came mixed from the two speakers that located together in one capsule or very close one to the other and it will heard like a mono sound that come out from form of one channel.

The invention suggest a system that capturing and guiding the unique sound from each one of the stereo speakers that packed together in closed box or located very close one to the other and guiding the unique sound hermetically from each speaker exclusively to the matched ear—the sound from the right speaker gets only to right ear and sound from the left speaker gets only to the left ear. The system includes devices that connected on each one of the stereo speakers as a cap. The device covers the speaker cones in hermetic way and guide the unique sound that coming out from the speaker directly to the user's ear through middle facility—such as air tubes. Using this system to conducting the sound from the speakers hermetically and directly to the user's ears will accomplish this non-obviousness result of hearing the sound as comes from various directions although the speakers are located together in one closed box or very close one to the other and we were expected that the sound will be mixed and not be heard as stereo.

Playing stereo sound in those speakers that located together in one closed capsule or that are located very near one to the other and away from the user ears, and using this sound guiding system, the unique sound from each one of the speakers will be captured hermetically and guided directly from the speaker with connector facility between the speakers and the user's ears—such as air tubes—and the sound will be transmitted exclusively to the user's matched ear—the sound from the right speaker gets only to right ear and sound from the left speaker gets only to the left ear—as at least two independent audio channels in such a way as to create the impression of sound heard from various directions, as in natural hearing. This invention can be used which any sound player like cell phone, MP3 player or any other kind of electronic device that produce stereophonic sound.

DETAILED DESCRIPTION OF THE INVENTION

Figure 1:
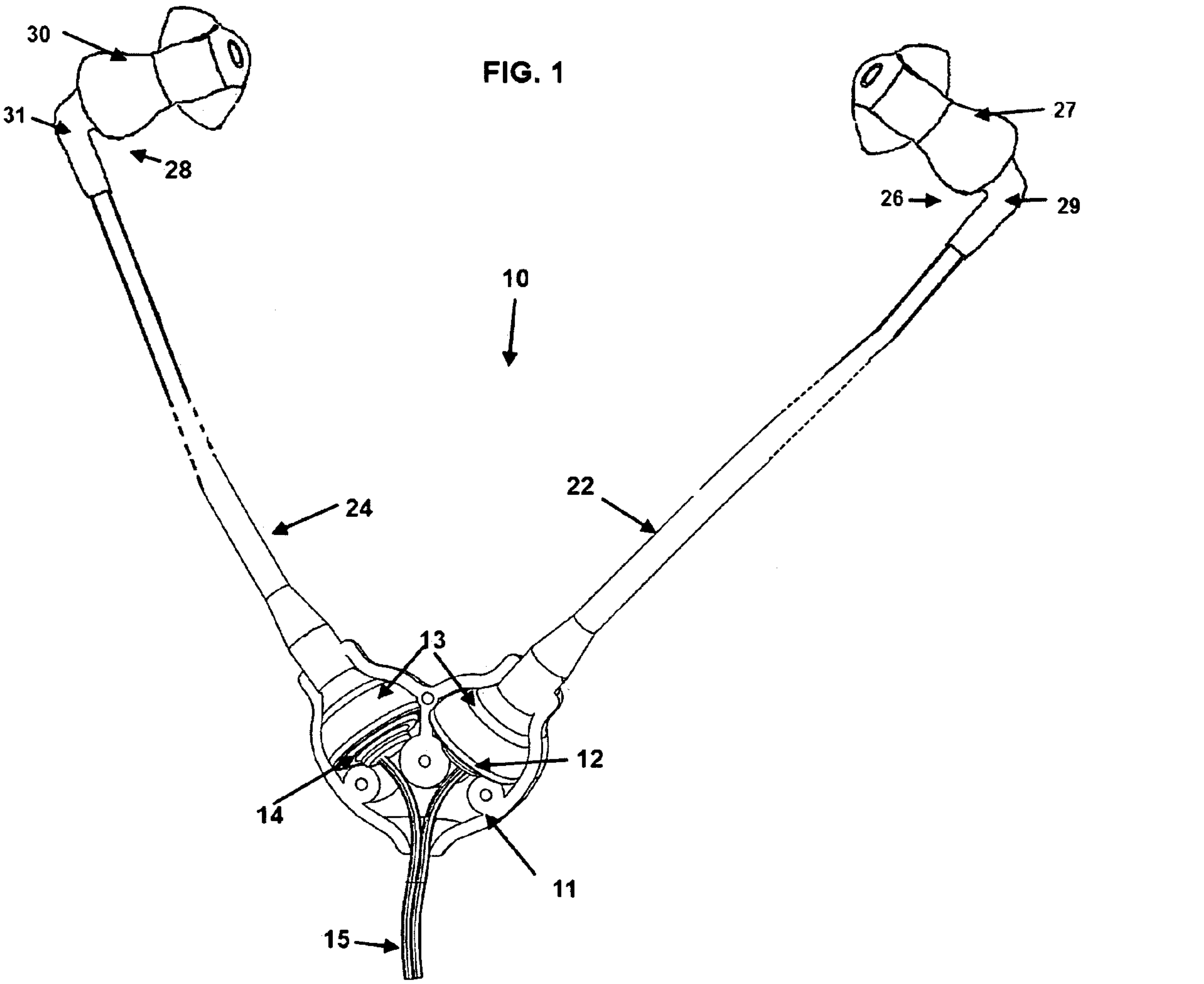
FIG. 1 is a perspective view of the stereo speaker packed in close capsule while the sound gets to the earpieces by hollow tube.

Referring to the drawings the headset indicated generally by the number 10, as illustrated in FIG. 1 including the stereo speakers—right speaker 12 and left speaker 14, and the hollow tubes that conducts the sound from the speaker to the user's ears. The right hollow tube 22 and the left hollow tube 24, the right earpiece 26 and the left earpiece 28.

The close capsule or box 11 which contains the stereo speakers 12 & 14 and the speaker caps 13 the device that covers the speaker cones hermetically and connected to the hollow tubes 22 & 24 which guide the sound to the earpieces 26 & 28. The close capsule 11 preferably takes the form illustrated in FIG. 2 and described in more particular detail hereinafter. The electric wires of the stereo speakers 15, which connect the speaker to the sound player like cell phone, MP3 player or any other kind of electronic device that produce stereophonic sound.

The earpieces 26 & 28 include the eartips 27 & 30 and a hollow connectors 29 & 31 that connect the eartips to the hollow tubes.

Figure 2:
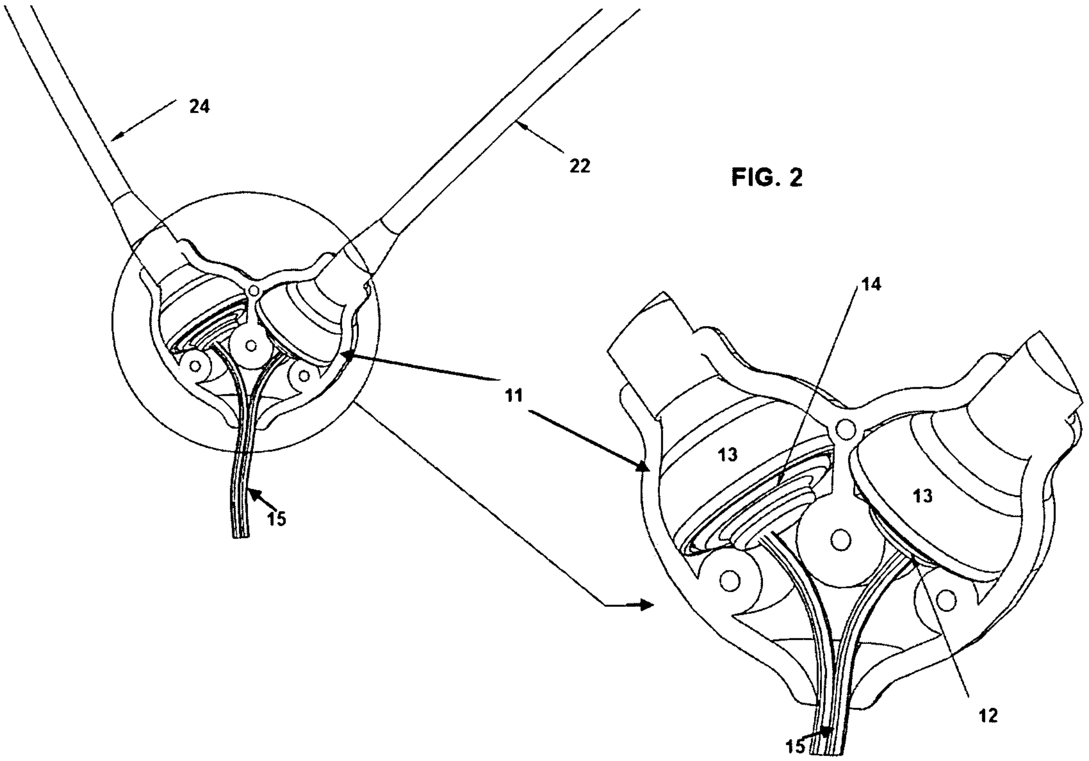
FIG. 2 is a detailed view of the stereo speaker inside the close capsule and the system facility of how to conduct the sound through hollow tube between the speakers and the user's ears.

The illustrated in FIG. 2 described in more particular detail the closed capsule or box that contain the set of stereo speakers 12 & 14 and the speaker caps 13 that that covers the speaker cones hermetically, capture the sound of each one of the speakers and guided it to the connected hollow tubes 22 & 24.

Figure 3:
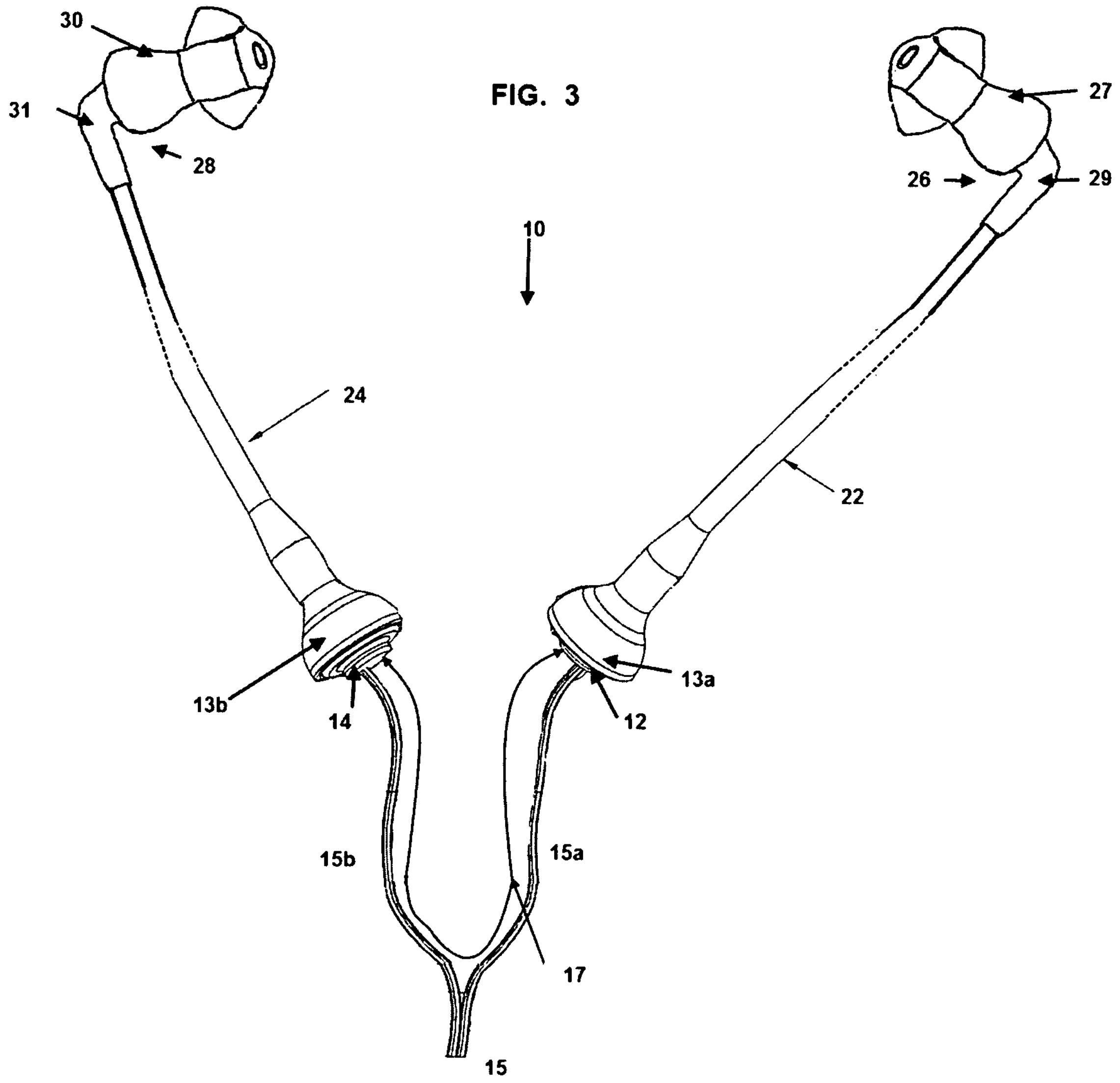
FIG. 3 is a perspective view of the stereo speakers located close one to the other and away from the user ears while the sound gets to the earpieces by hollow tube.

The illustrated in FIG. 3 described the design when the stereo speakers in more particular detail the closed capsule or box that contain the set of stereo speakers 12 & 14 and the speaker caps 13 that connect the hollow tubes to the speakers 12 & 14 doesn't packed together in one closed capsule as described in FIG. 1 & FIG. 2 but in return for, the speaker located close one to another with less the 10 cm or 20 cm distance between them 17 and away from the user ears as describe hereinafter in claims 8. & 9. Each one of the stereo speakers 12 & 14 connect to the matched hollow tube (Sound from the right speaker to tube and sound from the left speaker to the left tube) by speaker caps 13*a* & 13*b*. The caps closed hermetic on the speaker to catch the maximized as possible sound from the speaker and conduct it to the user ear through the hollow tubes 22 & 24.

While the present invention has shown and described with reference to specific exemplar forms only, it will be apparent to those skilled in the art that it is not so limited but is susceptible to various changes and modifications without departing from the spirit and scope thereof.

What I claim is:

1. A system for capturing and guiding stereophonic sound, comprising:

a first stereo speaker for receiving electronic signals from a first audio channel, the first stereo speaker including a first diaphragm, a first cap covering the first diaphragm of the first stereo speaker, the first cap in fixed relation to the first stereo speaker;

a second stereo speaker for receiving electronic signals from a second audio channel while the first stereo speaker is receiving different electronic signals from the first audio channel, the second stereo speaker including a second diaphragm, the first audio channel comprising audio that is different from the audio comprised by the second audio channel, a second cap covering the second diaphragm of the second stereo speaker, the second cap in fixed relation to the second stereo speaker;

an enclosed capsule housing the first and second stereo speakers;

a first sound carrying tube, one end of the first sound carrying tube operatively engaged to the first diaphragm and a second end of the first diaphragm connected to a left earpiece, the first sound carrying tube for carrying sound from the first speaker to the left earpiece so as to extend the first audio channel from the first stereo speaker to the left earpiece, the first sound carrying tube configured to distance the first stereo speaker and the first cap from a left ear of a user;

a second sound carrying tube, one end of the second sound carrying tube operatively engaged to the second diaphragm and a second end of the second diaphragm connected to a right earpiece, the second sound carrying tube for carrying sound from the second speaker to the right earpiece so as to extend the second audio channel from the second stereo speaker to the right earpiece, the second sound carrying tube configured to distance the second stereo speaker and the second cap from a right ear of the user, the first stereo speaker and the first cap configured such that, independent of the enclosed capsule that houses the first and second stereo speaker, sound entering the first stereo speaker and exiting the first diaphragm is acoustically isolated from the second stereo speaker, sound that has exited the first diaphragm remains acoustically isolated from the second stereo speaker while traveling through the first sound carrying tube to the first earpiece, the second stereo speaker and the second cap configured such that, independent of the enclosed capsule that houses the first and second stereo speaker, sound entering the second stereo speaker and exiting the second diaphragm is acoustically isolated from the first stereo speaker, sound that has exited the second diaphragm remains acoustically isolated from the first stereo speaker while traveling through the second sound carrying tube to the second earpiece, the system configured such that when the user wears the left earpiece in the left ear and the right earpiece in the right ear the audio of the first channel from the left earpiece is audible by the left ear of the user but not the right ear while the audio of the second channel from the right earpiece is simultaneously audible by the right ear of the user so that stereophonic sound is audible by the user, the audio of the second channel not being audible by the left ear.

2. The system of claim 1, wherein the first stereo speaker together with the first sound carrying tube comprise a first component of the system, the second stereo speaker together with the second sound carrying tube comprise a second component of the system, wherein the first component and the second component are acoustically isolated from one another.

3. The system of claim 1, wherein the first channel and the second channel comprise wires that transmit stereophonic sound outputted from an electronic device.

4. The system of claim 1, wherein the first and second sound carrying tubes are hollow.

5. The system of claim 1, wherein the system outputs two independent audio channels, thereby creating an impression to a wearer of the left and right earpieces, of sound coming from multiple directions.

6. The system of claim 1, wherein the first and second stereo speakers are close enough together in the enclosed capsule that the first and second caps are adjacent to one another.

7. The system of claim 1, wherein the first cap captures and guides sound from the first stereo speaker to the first sound carrying tube and wherein the second cap captures and guides sound from the second stereo speaker to the second sound carrying tube.

8. The system of claim 1, wherein the first diaphragm transmits sound substantially only to the first sound carrying tube and wherein the second diaphragm transmits sound substantially only to the second sound carrying tube.

9. The system of claim 1, wherein the first and second sound carrying tubes are hollow.

10. The system of claim 1, wherein, the enclosed capsule is separate from at least one of the first sound carrying tube and the second sound carrying tube.

11. The system of claim 10, wherein the enclosed capsule is separate from both the first and second sound carrying tubes.

12. The system of claim 1, wherein at least one of "(i) and "(ii) is true:

(i) the first sound carrying tube is configured to distance the first stereo speaker and the first cap from the left ear of the user by at least a length of the first sound carrying tube; and (ii) the second sound carrying tube is configured to distance the second stereo speaker and the second cap from the right ear of the user by at least a length of the second sound carrying tube.

13. The system of claim 12, wherein the first sound carrying tube is configured to distance the first stereo speaker and the first cap from the left ear of the user by at least a length of the first sound carrying tube; and wherein the second sound carrying tube is configured to distance the second stereo speaker and the second cap from the right ear of the user by at least a length of the second sound carrying tube.

14. The system of claim 1, wherein the one end of the first sound carrying tube operatively engaged to the first diaphragm is sealingly attached to the first stereo speaker.

15. A system for capturing and guiding stereophonic sound, comprising:

a first stereo speaker for receiving electronic signals from a first audio channel, the first stereo speaker including a first diaphragm, a first cap covering the first diaphragm of the first stereo speaker; the first cap in fixed relation to the first stereo speaker, a second stereo speaker for receiving electronic signals from a second audio channel while the first stereo speaker is receiving different electronic signals from the first audio channel, the second stereo speaker including a second diaphragm, the first audio channel comprising audio that is different from the audio comprised by the second audio channel, a second cap covering the second stereo speaker; the second cap in fixed relation to the second stereo speaker, the first and second speakers separated by a distance of less than twenty centimeters from one another;

a first sound carrying tube, one end of the first sound carrying tube operatively engaged to the first diaphragm and a second end of the first diaphragm connected to a left earpiece, the first sound carrying tube for carrying sound from the first speaker to the left earpiece so as to extend the first audio channel from the first stereo speaker to the left earpiece, the first sound carrying tube configured to distance the first stereo speaker and the first cap from a left ear of a user; and a second sound carrying tube, one end of the second sound carrying tube operatively engaged to the second diaphragm and a second end of the second diaphragm connected to a right earpiece, the second sound carrying tube for carrying sound from the second speaker to the right earpiece so as to extend the second audio channel from the second stereo speaker to the right earpiece, the second sound carrying tube configured to distance the second stereo speaker and the second cap from a right ear of the user, the first stereo speaker and the first cap configured such that, independent of the distance between the first and second stereo speakers, sound entering the first stereo speaker and exiting the first diaphragm is acoustically isolated from the second stereo speaker, sound that has exited the first diaphragm remains acoustically isolated from the second stereo speaker while traveling through the first sound carrying tube to the first earpiece, and the second stereo speaker and the second cap configured such that, independent of the distance between the first and second stereo speakers, sound entering the second stereo speaker and exiting the second diaphragm is acoustically isolated from the first stereo speaker, sound that has exited the second diaphragm remains acoustically isolated from the first stereo speaker while traveling through the second sound carrying tube to the second earpiece, the system configured such that when the user wears the left earpiece in the left ear and the right earpiece in the right ear the audio of the first channel from the left earpiece is audible by the left ear of the user but not the right ear while the audio of the second channel from the right earpiece is simultaneously audible by the right ear of the user so that stereophonic sound is audible by the user, the audio of the second channel not being audible by the left ear.

16. The system of claim 15, wherein the first stereo speaker together with the first sound carrying tube comprise a first component of the system, the second stereo speaker together with the second sound carrying tube comprise a second component of the system, wherein the first component and the second component are acoustically isolated from one another.

17. The system of claim 15, wherein the first and second stereo speakers are within ten centimeters of one another.

18. The system of claim 15, wherein the first channel and the second channel comprises wires that transmit stereophonic sound outputted from an electronic device.

19. The system of claim 15, wherein the first and second sound carrying tubes are hollow.

20. The system of claim 15, wherein the first diaphragm transmits sound substantially only to the first sound carrying tube and wherein the second diaphragm transmits sound substantially only to the second sound carrying tube.

21. The system of claim 15, wherein the system outputs two independent audio channels, thereby creating an impression to a wearer of the left and right earpieces, of sound coming from multiple directions.

22. The system of claim 15, wherein the first cap captures and guides sound from the first stereo speaker to the first sound carrying tube and wherein the second cap captures and guides sound from the second stereo speaker to the second sound carrying tube.

23. The system of claim 15, wherein at least one of "(i) and "(ii) is true:

(i) the first sound carrying tube is configured to distance the first stereo speaker and the first cap from the left ear of the user by at least a length of the first sound carrying tube; and (ii) the second sound carrying tube is configured to distance the second stereo speaker and the second cap from the right ear of the user by at least a length of the second sound carrying tube.

24. The system of claim 23, wherein the first sound carrying tube is configured to distance the first stereo speaker and the first cap from the left ear of the user by at least a length of the first sound carrying tube; and wherein the second sound carrying tube is configured to distance the second stereo speaker and the second cap from the right ear of the user by at least a length of the second sound carrying tube.

25. The system of claim 15, wherein the one end of the second sound carrying tube operatively engaged to the second diaphragm is sealingly attached to the second stereo speaker.

* * * * *